US006335374B1

(12) United States Patent
Kuusisto et al.

(10) Patent No.: US 6,335,374 B1
(45) Date of Patent: Jan. 1, 2002

(54) PENETRATING PROTECTANT

(75) Inventors: Eeva-Liisa Kuusisto, Livingston; Timothy Savage, Sparta; Peter Schaeufele, Ringwood, all of NJ (US); Rudi Moerck, Ponte Vedra Beach, FL (US)

(73) Assignee: Troy Technology Corporation, Inc., Wilmington, DE (US)

( * ) Notice: Subject to any disclaimer, the term of this patent is extended or adjusted under 35 U.S.C. 154(b) by 0 days.

(21) Appl. No.: 08/320,186

(22) Filed: Oct. 7, 1994

(51) Int. Cl.$^7$ .................. A61K 47/32; A61K 31/74; A01N 25/00; A01N 59/22
(52) U.S. Cl. .............. 514/772.4; 514/946; 424/78.31; 424/405; 424/668
(58) Field of Search ............... 424/78.09, 409, 424/78.81, 405; 514/772.4, 946

(56) References Cited

U.S. PATENT DOCUMENTS

| | | |
|---|---|---|
| 2,551,387 A | 5/1951 | Moffett et al. |
| 3,227,563 A | * 1/1966 | Fahlstrom ............... 424/78.09 |
| 3,923,870 A | 12/1975 | Singer |
| 4,028,291 A | 6/1977 | Tsuchiya et al. |
| 4,276,211 A | 6/1981 | Singer et al. |
| 4,297,258 A | 10/1981 | Long, Jr. |
| 4,330,448 A | 5/1982 | Iwata |
| 4,844,891 A | 7/1989 | Rosen et al. |
| 4,977,186 A | 12/1990 | Gruening |
| 5,228,905 A | 7/1993 | Grunewalder et al. |
| 5,288,805 A | 2/1994 | Kodali |

FOREIGN PATENT DOCUMENTS

EP   0 258 030   2/1988

OTHER PUBLICATIONS

"Newcowel FLE", Ashland–Sudchemie–Kernfest, GmBh, Germany (1992).
"Wood Protection for Today's Environment", Jane Yuster, Product Manager and Manager of Toxicology and Registration, Troy Chemical Corporation, Newark, NJ (1984).

\* cited by examiner

Primary Examiner—Thurman K. Page
Assistant Examiner—Blessing Fubara
(74) Attorney, Agent, or Firm—Banner & Witcoff, Ltd.

(57) ABSTRACT

A penetrating concentrate containing a biocidal amount of a biocide uses a penetrating carrier vehicle containing an emulsifiable copolymer of a cyclic diene and a polymerizable, unsaturated glyceride. For biocides, such as iodopropargyl carbamate, which otherwise requires use of significant amounts of co-solvent to disperse, is directly soluble in the copolymer thereby eliminating or at least substantially reducing the need for co-solvents to assure stability of the biocide in the formulation. The concentrate also exhibits a low level of volatile organics.

13 Claims, No Drawings

PENETRATING PROTECTANT

FIELD OF THE INVENTION

The invention relates to a rapidly penetrating concentrate containing biocides that do not require significant amounts of co-solvents to stabilize the biocide.

BACKGROUND OF THE INVENTION

Many architectural and exposed wood surfaces are treated with biocides (a term that includes fungicides, algacides, and insecticides) or other preservatives for protection. Such treatments are typically applied in the form of a penetrating liquid. Generally, these materials are first prepared as a preservative concentrate or concentrate emulsion. The concentrate or concentrate emulsion is then added to a compatible binder along with other components to form either a non-filmforming protectant or a filmforming coating.

A number of biocides and related biocides are used to protect wood against attack. One of the well accepted class of biocides are the iodopropargyl carbamates with 3-iodo-2-propynyl butyl carbamate ("IPBC", CAS No. 55406-53-6) and compounds derived therefrom being the most recognized. IPBC is commercially available in a formulated liquid form from Troy Corporation under the trademark TROYSAN POLYPHASE®. These compounds and their preparation are well described in U.S. Pat. No. 3,923,870; EP 257,888; EP 258,030; and Hansen, "IPBC—A New Biocide for Wood Protection", *Modern Paint and Coatings*, November 1984, the disclosures of which are herein incorporated by reference.

Iodopropargyl carbamates have found wide commercial acceptance in paint films; penetrating protectants and stains for wood, leather, paper, cloth, and other materials; adhesives; caulks; paper and plastics coatings; personal care products; and similar filmforming or non-filmforming products. For wood preservatives, IPBC must be present in a concentration of at least 0.5% by total weight to provide biocidal protection. Products like paints or stains should contain IPBC in a quantity within the range of 0.05–0.5% by total weight to provide biocidal protection.

Pure IPBC is a crystalline solid that is insoluble in a wide variety of liquids, as necessary for an effective biocide. Unless products containing IPBC are, however, properly formulated to provide solution stability to the IPBC, tiny needle crystals fall out of solution as the product dries significantly affecting general biocidal protection. See, Hansen, "IPBC—A New Biocide for Wood Protection", *Modern Pain and Coatings* (November 1984).

Preservative concentrates of IPBC have traditionally been made with high quantities of one or more co-solvents to provide stability to the IPBC as well as provide a liquid that is soluble in conventional binders. See, e.g., the examples of U.S. Pat. No. 4,276,211 (dipropylene glycol and diacetone alcohol) and U.S. Pat. No. 4,977,186 (co-solvent of ethylglycol acetate or methoxypropyl acetate in water/mineral spirits vehicle). In general, a solvent would be used to dissolve the IPBC, and a co-solvent would be added to stabilize the IPBC/solvent solution in the final preservative formulation. TROYSAN® POLYPHASE® AF-1 is a commercial IPBC concentrate that has about 40% IPBC by weight and employs 35 wt % of a co-solvent system of dimethylsulfoxide, high flash naphtha, and dipropylene glycol.

Aside from the added expense, high levels of co-solvents are diluents in the final product, inherently serve to limit the solids concentration that can be prepared, and are a source of volatile organic materials.

It would be useful to have an biocide concentrate for IPBC and structurally similar biocides that would not require high quantities, if any, of co-solvents yet maintain compatibility with the main binder systems used in commercial coatings. In combination, it would be helpful to be able to provide a biocide concentrate that exhibits levels of solubilized, stable biocide that are greater than 2% by total weight of formulated products.

As a complicating factor, binder and carrier systems are under continuing pressure to employ materials with a low volatile organics content (VOC). The emissions from each component of a product formulation will contribute to the total VOC of the product. Even aqueous systems must be concerned about VOC levels.

It would be desirable to have a iodopropargyl carbamate preservative concentrate that exhibited low VOC levels.

Penetration below the surface of a porous substrate is important for providing effective levels of fungus protection. This is particularly true for wood. Unfortunately, aqueous preservative formulations have traditionally been less effective at penetration than nonaqueous solvent-based formulations. For side grain penetration, water in the formulation swells the wood fibers which shrink the interfiber passages and hinder further penetration.

It would be helpful to have an aqueous protectant for wood with high penetration and fungus protection.

SUMMARY OF THE INVENTION

It is an objective of the invention to provide an emulsifiable biocide formulation that exhibits reduced or eliminated levels of co-solvents for the biocide yet is compatible with alkyd binder systems used in commercial coatings.

It is an objective of the invention to provide a biocidal concentrate with low levels of co-solvent.

It is an objective of the invention to supply a biocidal concentrate that exhibits low VOC levels.

A still further objective of the invention is to provide an aqueous protectant for wood with high penetration and fungus protection.

In accordance with these and other objectives of the invention that will become apparent from the description herein, the invention provides a penetrating biocide concentrate comprising and, preferably, consisting essentially of:

(a) a biocidal amount of a biocidal compound within the general formula:

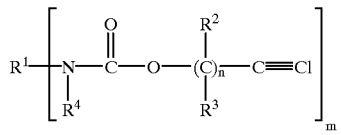

and (b) a penetrating carrier comprising a cyclic diene crosslinked polymerizable, unsaturated glyceride wherein said concentrate contains less than 35% by weight of added co-solvents for the biocidal compound.

The penetrating biocide concentrate of the invention provides a vehicle for delivering effective amounts of biocide to porous substrates with low VOC in aqueous and nonaqueous protectant systems. On wood, products with the concentrate penetrate the wood surface deeply and provide a high level of biocidal protection. The concentrate can be used directly as a non-filmforming preservative or added as the preservative component in a filmforming coating product.

DETAILED DESCRIPTION

The present invention is a penetrating biocide concentrate containing (a) a biocidal amount of a biocidal compound within the general formula:

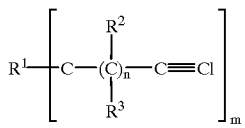

and (b) a penetrating carrier of a copolymer of a cyclic diene, wherein the concentrate contains levels of co-solvents for the carbamate that are less than otherwise needed in the absence of the penetrating carrier. The penetrating carrier enables low VOC, aqueous or nonaqueous systems to carry iodopropargyl carbamate into porous substrates for protection against fungus attack. The penetrating carrier is particularly useful on cellulosic substrates. The carrier of the invention penetrates deeply into the wood without external pressures or vacuum.

In general, the active biocides useful in the concentrate of the present invention are compounds included within the broadly useful class of compounds within generic Formula I:

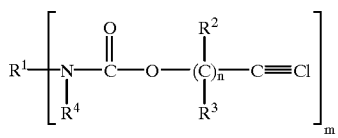

Most preferred are iodopropargyl carbamates which follow Formula II:

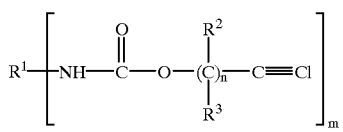

wherein, for each formula:

$R^1$ is alkyl, substituted or unsubstituted aryl, or substituted or unsubstituted alkaryl of one to twenty carbon atoms and having 1 to 3 linkages corresponding to m;

$R^2$ and $R^3$ are independently selected from hydrogen or methyl;

m and n are independently selected integers from 1 to about 3; and $R^4$ is selected from hydrogen and $R^1$.

When $R^1$ is an aryl or alkaryl, the aryl group will have the general formula:

wherein:

X is cyano, nitro, lower alkyl, halogenated lower alkyl, alkoxy of 1–12 carbon atoms unsubstituted or substituted with lower alkyl groups, lower alkenyloxy, unsubstituted or halogenated lower alkynoxy, lower alkoxycarbonyl, or lower alkylthio;

p is zero or an integer of 1 to 6;

n is zero or an integer of 1 to 4; and the sum of m+n is less than 6.

The preferred biocide is 3-iodo-2-propynyl butyl carbamate.

A biocidally effective amount of biocidally active compound is used in the concentrate to provide protection against attack by fungus, algae, or insects (depending on the specific biocide employed) when applied to the target substrate. The specific amount of biocide applied as a protectant in the final formulation will depend on the specific product, substrate, and environment. Generally, it is sufficient to apply at least enough biocide as is conventional in the art to supply a biocidal efficacy. For fungicides, the amount of applied fungicide will generally be within the range from, based on an activity relative to 3-iodo-2-propynyl butyl carbamate, about 0.05–0.4 kilogram per square meter (kg/$m^2$), preferably about 0.1–0.2 kg/$m^2$. Higher concentrations of biocide can be applied without detrimental effect. Concentrates according to the invention will generally contain up to about 4–5% fungicide, preferably about 1–5% fungicide, and even more preferably about 3–5% fungicide.

The penetrating carrier vehicle used in the present invention is a water emulsifiable, non-filmforming, copolymer in which the biocide is at least 3 wt % soluble. Such copolymers are the result of a polymerization reaction of a cyclic diene, preferably cyclopentadience, and a polymerizable unsaturated glyceride oil. Exemplary glyceride oils such as linseed oil (CAS No. 8001-26-1), marine oil, tung oil, and dehydrated castor oil.

The copolymer preferably is made of 70–90 wt % glyceride oil and 10–30 wt % cyclic diene. When the glyceride is linseed oil, the copolymer is preferably made according to the copolymerization process in U.S. Pat. No. 5,288,805 with 70–90 wt % of a linseed oil exhibiting an iodine value of 170–195 and 10–30 wt % cyclopentadiene to make a copolymer having a viscosity of 500–10,000 cps at 25° C. and an average molecular weight within the range of 1200–2600. The copolymerization is conducted at 200°–300° C. for 1–48 hours until the desired viscosity is produced. The disclosure of U.S. Pat. No. 5,288,805 is herein incorporated by reference.

Copolymers of glyceride oils (such as linseed or soya bean oil) and cyclic diene hydrocarbons (e.g., cyclopentadiene) have hitherto been known as useful for filmforming binders for pigments and useful in the fields of adhesives, inks, paints, coatings, and rubber compounding. See, U.S. Pat. Nos. 2,551,387 and 4,330,448 the disclosures of which are herein incorporated by reference. Penetrating carrier vehicles useful in the present invention are commercially available under the tradenames NEWCOWEL™ FLE or NEWCOWEL™ FLE-55 (emulsion form), sold by Ashland-Südchemie-Kernfest Gmbh (4010 Hilden, Reisholzstrasse 16, Germany) and DILULIN™ sold by Cargill, Inc. (Technical Oils Dept., Minneapolis, Minn. USA).

The penetrating biocide concentrate of the invention can be used as the sole binder for a non-film forming coating as well as the protective component in paint films and penetrating protectants and stains for wood, leather, paper, cloth, and other porous materials. Because the amount of co-solvents is significantly reduced or eliminated altogether, penetrating protective compositions according to the present invention can be made to carry greater than 30% solids, preferably about 50 to 100%, and more preferably about 80–98% by weight of solids based on the total weight of the coating product.

The concentrate of the invention can also be added to aqueous systems by first forming an emulsified concentrate. Emulsification can be by any conventional method with convention emulsification equipment. See, e.g., U.S. Pat. No. 5,228,905. Suitable devices emulsify with high shear conditions from impinging fluid streams or through ultrasonic energy.

Some amount of co-solvent may be useful to enhance the stability of the biocides in aqueous systems. Suitable co-solvents that can be used include dimethylsulfoxide, high flash naphtha, dipropylene glycol, mono- and dialkyl ethers of ethylene glycol and their derivatives (e.g., Cellosolve™ (ethylene glycol monoethyl ether), butyl Cellosolve™, butyl Cellosolve™ acetate, Cellosolve™ acetate, dibutyl Cellosolve™, n-hexyl Cellosolve™, methyl Cellosolve™, methyl Cellosolve™ acetate, and phenyl Cellosolve™), TEXANOL™, hexylene glycol, toluene, propylene glycol mono t-butyl ether, tripropylene glycol monomethyl ether, propylene glycol monomethyl ether acetate, mono-and dialkyl ethers of diethylene glycol and their derivatives (e.g., Carbitol™ (diethylene glycol monoethyl ether), butyl Carbitol™, butyl Carbitol™ acetate, Carbitol™ acetate, dibutyl Carbitol™, diethyl Carbitol™, N-hexyl Carbitol™, methyl Carbitol™, and methyl Carbitol™ acetate), dipropylene glycol mono methyl ether, DOWANOL™ PNB, isopropyl alcohol, butyl diglycol, COASOL™ and mixtures thereof.

If co-solvents are employed, concentrates made in accordance with the invention will include less than 35 wt % of such co-solvents, preferably 0–30 wt %, and even more preferably 0–25 wt % co-solvents. Particularly preferred is a penetrating biocide concentrate according to the invention that employs 0–10 wt % co-solvents for stabilizing the biocide in the polymeric binder of the invention.

One or more adjuvants can be used in products made with the present concentrate without materially affecting the solvation relationship between the polymeric carrier and the biocide. Preservative products can also include water sheathing agents (e.g., polytetrafluoroethylene), waterproofimg agents, organic binding agents (e.g., long oil alkyds), additional biocides, auxiliary solvents, processing additives, fixatives, plasticizers, UV stabilizers, dispersion stability enhancers, water soluble or insoluble dyes, white and color pigments or pigment dispersions, corrosion inhibitors, anti-settling agents, drying agents, olefin or paraffin waxes that enhance water beading, and anti-skinning agents as well as any other conventional additive for such products. Water emulsifiable drying agents are preferably added to the formulation before emulsification. In aqueous systems, an emulsifier having an HLB value of at least 10 is preferably used. More preferred are emulsifiers with an HLB value of about 11. Suitable penetrating protective compositions are described in commonly owned, copending U.S. patent application Ser. No. 08/132,769 filed on Jul. 11, 1994 the disclosure of which is herein incorporated by reference.

A particularly preferred formulation includes 0.05–1 wt % fumed silica as a waterproofing and dispersion stability enhancer, 5–40 wt % mineral spirits to control the viscosity for ease of application, 0.01–2 wt % of a water sheathing agent such as paraffin waxes, polyolefins, and fluoropolymers as a water sheathing agent, 75–95% penetrating copolymer carrier, 0.01–5 wt % technical grade iodopropargyl carbamate (preferably IPBC), and 0.01–1 wt % of an inorganic ultraviolet protectant. This formulation exhibits deep, rapid penetration of unsealed wood surfaces thereby allowing the carrier to carry biocidally effective amounts of IPBC deeply into the wood for protection thereof.

Compositions containing the concentrate according to the invention can be applied by any conventional method. Such methods include dipping, flow coating, roll coating, brushing, wiping, and the like.

EXAMPLES

Example 1

A penetrating protectant having the materials in Table 1 is prepared.

TABLE 1

| Ingredient | Functionality | Concentration (wt %) |
| --- | --- | --- |
| Fumed silica | waterproofing, dispersion stabilizer | 0.3 |
| Mineral spirits | viscosity reduction | 15.0 |
| Water sheathing agent | water sheathing agent | 0.3 |
| Copolymer penetrating carrier (Newcowel ™ FLE) | | 83.9 |
| 3-iodo-2-propynyl butyl carbamate | | 0.3 |
| Inorganic UV protectant | | 0.2 |

The formulation is prepared by initially forming a concentrate of the biocide in the copolymer reserving a small amount of copolymer for forming a paste of the UV protectant, the silica, and the water sheathing agent in some of the copolymer. For viscosity control and improved wetting, a small quantity of the mineral spirits may also be used. Thereafter, the mineral spirits and biocide concentrate are added and mixed together until a homogeneous dispersion is formed. This formulation can then be used as a non-filmforming protectant for wood.

What is claimed is:

1. A nonaqueous, emulsifiable, penetrating biocidal concentrate consisting essentially of: (a) a biocidal amount of a compound within the general formula:

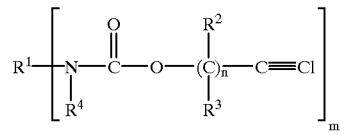

wherein:
R$^1$ is alkyl, substituted or unsubstituted aryl, or substituted or unsubstituted alkaryl of one to twenty carbon atoms and having 1 to 3 linkages corresponding to m;
R$^2$ and R$^3$ are independently selected from hydrogen or methyl;
m and n are independently selected integers from 1 to about 3; and
R$^4$ is selected from R$^1$ and hydrogen; and
(b) a wood penetrating carrier in which the biocide compound is at least 3 wt % soluble comprising a copolymer of a cyclic diene and an unsaturated, polymerizable glyceride wherein said concentrate contains 0–10% by weight of added co-solvents for the biocidal compound.

2. A concentrate as in claim 1 consisting essentially of: (a) a biocidal amount of a compound within the general formula:

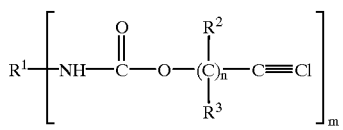

wherein:
R¹ is alkyl, substituted or unsubstituted aryl, or substituted or unsubstituted alkaryl of one to twenty carbon atoms and having 1 to 3 linkages corresponding to m;
R² and R³ are independently selected from hydrogen or methyl; and
m and n are independently selected integers from 1 to about 3;
(b) a wood penetrating carrier comprising a copolymer of 10–30 wt % of a cyclic diene and 70–90 wt % of an unsaturated, polymerizable glyceride and having a viscosity of 500–10,000 cps at 25° C., wherein said concentrate contains no co-solvents for the biocidal compound.

3. A concentrate as in claim 1 consisting essentially of: (a) a biocidal amount of 3-iodo-2-propynyl butyl carbamate, and (b) a penetrating carrier comprising a copolymer of linseed oil and/or marine oil and cyclopentadiene.

4. A nonaqueous penetrating protectant formulation containing
(a) mineral spirits; and
(b) a wood penetrating biocidal concentrate consisting essentially of: (i) a biocidal amount of a compound within the general formula:

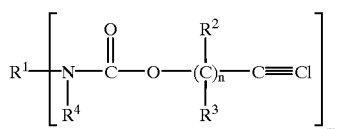

wherein:
R¹ is alkyl, substituted or unsubstituted aryl, or substituted or unsubstituted alkaryl of one to twenty carbon atoms and having 1 to 3 linkages corresponding to m;
R² and R³ are independently selected from hydrogen or methyl;
m and n are independently selected integers from 1 to about 3; and R⁴ is selected from R¹ and hydrogen; and
(ii) a wood penetrating carrier in which the biocide compound is at least 3 wt % soluble and comprising a copolymer of a cyclic diene and an unsaturated, polymerizable glyceride wherein said concentrate contains 0–10% by weight of co-solvent for the biocidal compound based on the weight of said concentrate.

5. A penetrating protectant according to claim 4 consisting essentially of:
a waterproofing and dispersion stability enhancer,
5–40 wt % mineral spirits,
0.01–2 wt % of a water sheathing agent,
75–95% of said penetrating carrier having a viscosity of 500–10,000 cps at 25° C. and an average molecular weight within the range of 1200–2600 made from 70–90 wt % of a linseed oil exhibiting an iodine value of 170–195 and 10–30 wt % cyclopentadiene,
0.01–5 wt % technical grade iodopropargyl carbamate, and
0.01–1 wt % of an inorganic ultraviolet protectant.

6. A concentrate according to claim 1, wherein the biocide compound is a fungicide and said concentrate has about 1–5% of said fungicide.

7. A concentrate according to claim 1, wherein said penetrating carrier is a water emulsifiable, non-filmforming, copolymer.

8. A concentrate according to claim 1 wherein said penetrating carrier is a copolymer of 70–90 wt % glyceride oil and 10–30 wt % cyclic diene.

9. A concentrate according to claim 1 wherein said penetrating carrier is a copolymer having a viscosity of 500–10,000 cps at 25° C. and an average molecular weight within the range of 1200–2600 made from 70–90 wt % of a linseed oil exhibiting an iodine value of 170–195 and 10–30 wt % cyclopentadiene.

10. A penetrating protectant according to claim 4 having greater than 30 wt % solids.

11. A penetrating protectant according to claim 4 having 50–100 wt % solids.

12. A penetrating protectant according to claim 4 having about 80–98 wt % solids.

13. A penetrating protectant according to claim 4 consisting essentially of:
5–40 wt % mineral spirits;
75–95 wt % of said penetrating carrier having a viscosity of 500–10,000 cps at 25° C. and an average molecular weight within the range of 1200–2600;
0.01–5 wt % technical grade iodopropargyl carbamate; and
0 wt % co-solvent for said iodopropargyl carbamate.

* * * * *